United States Patent [19]
Fishbine et al.

[11] Patent Number: 5,230,025
[45] Date of Patent: Jul. 20, 1993

[54] METHOD AND APPARATUS FOR CAPTURING SKIN PRINT IMAGES

[75] Inventors: Brian H. Fishbine, Albuquerque, N. Mex.; Glenn M. Fishbine, Eden Prairie, Minn.; Theodore D. Klein, Mound, Minn.; Daniel E. Germann, Bloomington, Minn.; Mark Ransom, Golden Valley, Minn.

[73] Assignee: Digital Biometrics, Inc., Minnetonka, Minn.

[21] Appl. No.: 575,796

[22] Filed: Aug. 31, 1990

[51] Int. Cl.⁵ ............................................. G06K 9/00
[52] U.S. Cl. .................................. 382/4; 382/5; 356/71
[58] Field of Search ................. 382/4, 5, 52, 54, 59; 356/71; 283/68, 69, 70

[56] References Cited

U.S. PATENT DOCUMENTS

| | | |
|---|---|---|
| 3,947,128 | 3/1976 | Weinberger et al. ............ 382/4 |
| 4,260,979 | 4/1981 | Smith ................................ 382/59 |
| 4,787,742 | 11/1988 | Schiller et al. ................... 382/5 |
| 4,811,414 | 3/1989 | Fishbine et al. ................. 382/5 |
| 4,827,527 | 5/1989 | Morita et al. .................... 382/4 |
| 4,933,976 | 6/1990 | Fishbine et al. ................. 382/5 |
| 4,944,021 | 7/1990 | Hoshino et al. ................. 382/5 |

Primary Examiner—Jose L. Couso
Attorney, Agent, or Firm—Merchant, Gould, Smith, Edell, Welter & Schmidt

[57] ABSTRACT

A system for generating data characteristic of a rolled skinprint in real time. A body part such as a finger contacts a receiving surface of an optical device. The receiving surface is imaged and recorded on an image recording medium during the period of contact. The resulting record is then used to generate digital data representative of the image of the skinprint. This is especially useful for recording a rolled fingerprint image taken on a flat receiving surface.

15 Claims, 6 Drawing Sheets

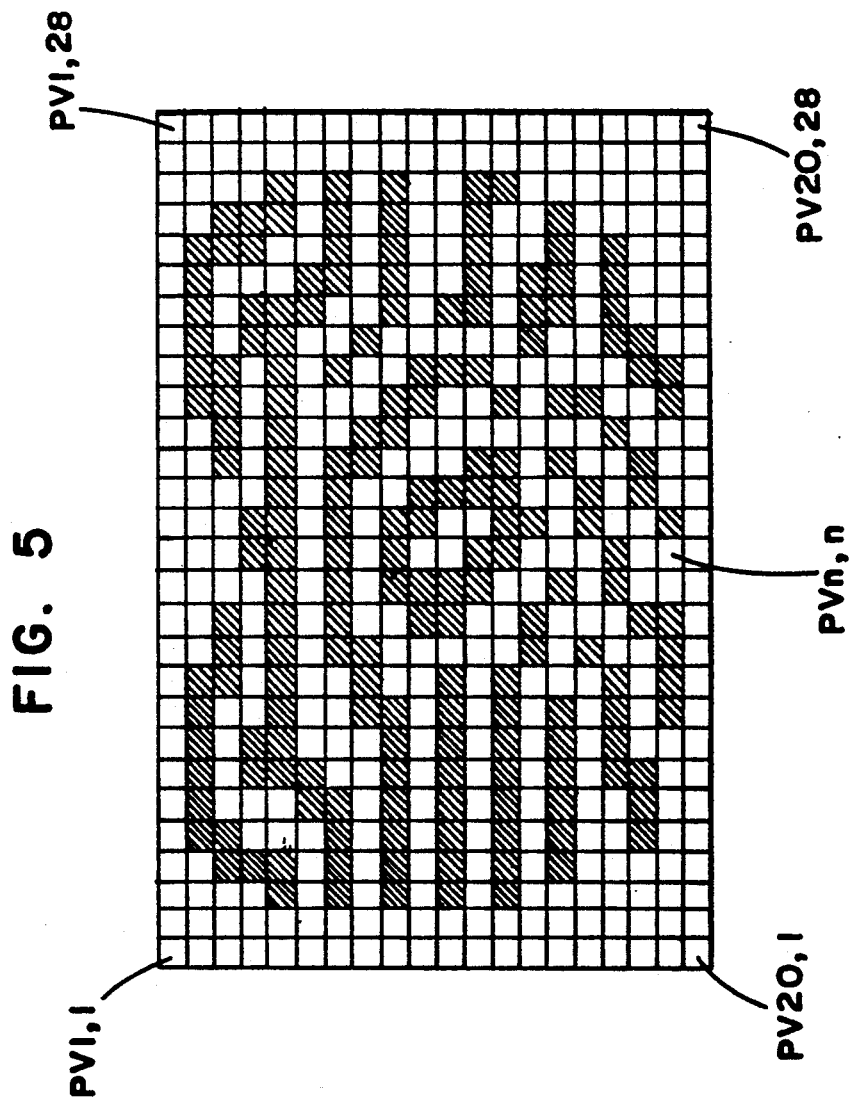

METHOD AND APPARATUS FOR CAPTURING SKIN PRINT IMAGES

BACKGROUND OF THE INVENTION

1. Field of the Invention

The present invention relates to computer processing of optical skin pattern images to produce rolled skin pattern images, especially fingerprint images.

2. Description of Background Material

Over the years, the most commonly used technique for obtaining "rolled" fingerprints has been to apply ink to the tip of individual fingers and roll the inked fingertips at an appropriate location on an applicant card. While these inking procedures will usually provide satisfactory images, they have their drawbacks. The inking procedure is messy. Several attempts are often required in order to obtain an acceptable fingerprint. Perhaps even a bigger drawback of this systems is that the printed images are not easily adaptable to computerized storage and processing techniques, inhibiting cooperation and fingerprint data transfer between various police agencies.

Systems which optically or optically and mechanically generate fingerprint images are also in use. Several such fingerprinting systems are disclosed in Fishbine et al. U.S Pat. No. 4,933,976, Ruell German Pat. No. 3423886 Al, Becker U.S. Pat. No. 3,482,498, McMahon U.S. Pat. No. 3,975,711, Schiller U.S. Pat. Nos. 4,544,267 and 4,322,163, and Marcus U.S. Pat. No. 4,553,837.

Due to the compound curved nature of the fingerprint on a finger, it is difficult to optically obtain an image of the fingerprint, especially an image corresponding to a rolled fingerprint. Fishbine et al. discloses a method based on building a composite image from a plurality of arrays of slice data characteristic of adjacent and overlapping two-dimensional slices of the fingerprint image.

The other references rely on complex mechanical movement of the fingerprint receiving optics. The Ruell patent discloses a fingerprinting system in which a camera images a finger rolled across a contact plate. Contact sensors on the edge of the plate provide information representative of which portion of the contact plate the finger overlies. The result is a plurality of adjacent but not overlapping two-dimensional slices that are pieced together to form the fingerprint image.

The Schiller patents disclose an apparatus in which a finger pressed against a platen provides a fingerprint object which is scanned by an interrogating beam of collimated light. The beam is linearly displaced across the platen thereby maintaining a constant angle between the interrogating light beam and the plane of the object being scanned. The Marcus U.S. Pat. No. 4,553,837 discloses a finger processing apparatus which includes a cylindrical-segment platen which supports a finger. Optical scanning equipment scans the circumference of the platen in such a manner that the angle of incidence of a light beam on the fingerprint object remains constant. The Becker U.S. Pat. No. 3,482,498 discloses several embodiments of an optical apparatus for producing a rolled fingerprint image. The embodiment shown in FIG. 1A utilizes a plurality of prisms and light sources, and produces only an approximation of the ball and side ridges. The embodiment shown in FIGS. 2 and 3 utilize a mechanical system actuated by a rolling finger to move and position a light source.

While the fingerprinting systems disclosed in the Ruell patent, the Marcus patent and the Becker patent may be capable of optically providing a rolled fingerprint image, these systems are less than wholly desirable. The mechanical aspects of these systems are relatively complicated. As a result, discontinuities, stray artifacts and other irregularities can appear in the composite image due to loss of focus or errors in merging the slices. The Fishbine et al. patent overcomes these problems but at the cost of requiring added computational power.

It is evident that there is a continuing need for improved optical fingerprinting systems. A system which can optically generate rolled fingerprint images in real time with limited computational requirements is desired. The system must of course be accurate and reliable.

SUMMARY OF THE INVENTION

The present invention is an improved method for generating data characteristic of a rolled skin pattern image, especially a fingerprint image. The image intensity summing properties of certain image recording media are used to build the rolled skin pattern image under controlled conditions. Images generated in accordance with this method will have image quality that is better and more reliable than the common ink method. The resulting system is simpler, less expensive and more reliable than competing optical or optical and mechanical devices. Generally, any skin print image such as those of the feet, hands, fingers, lips and the like can be recorded according to the invention. An especially preferred system is designed to record fingerprint images.

BRIEF DESCRIPTION OF THE DRAWINGS

FIGS. 5 is a graphical representation of the image shown in FIGS. 4C after being digitized by the digitizer shown in FIG. 1.

DETAILED DESCRIPTION OF THE PREFERRED EMBODIMENTS

In the following Detailed Description of the Preferred Embodiments, reference is made to the accompanying Drawings which form a part hereof, and in which is shown by way of illustration specific embodiments in which the invention may be practiced. It is to be understood that the other embodiments may be utilized and structural changes may be made without departing from the scope of the present invention.

Although the system of this invention can record the pattern of any skin surface, e.g., the foot, lips, hands or fingers, it is especially applicable to fingerprint images. Accordingly, the preferred embodiment focuses upon fingerprints but the principles, techniques and details apply to any skin print pattern.

Figure 1:
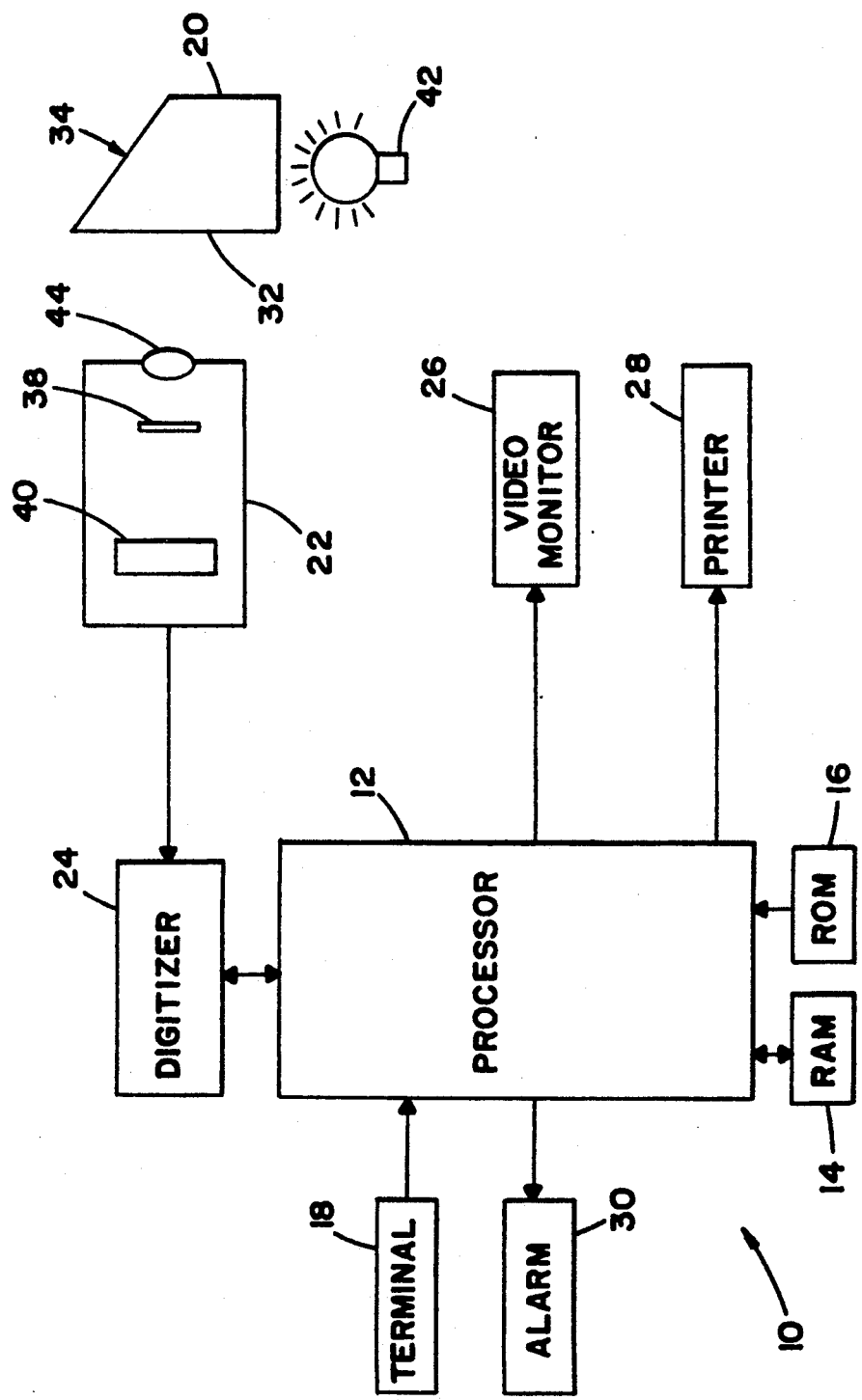
FIG. 1 is a block diagram representation of a system which can be used to generate rolled fingerprint images in accordance with the present invention.

A fingerprinting system 10 which can be used to optically produce rolled fingerprint images in accordance with the present invention is illustrated generally in FIG. 1. Fingerprinting system 10 is a microprocessor based system which includes processor 12 and associated random access memory (RAM) 14 and read only memory (ROM) 16. Image recorder 22, digitizer 24, video monitor 26, alarm 30, printer 28 and terminal 18 are interfaced to processor 12. Fingerprint images from the portions of a finger in contact with the receiving surface 34 as the finger is rolled across prism 20 are imaged by image recorder 22 and digitized by digitizer 24. An array of digital data representative of the fingerprint image is provided to processor 12. Image recorder 22 will include a lens, shutter mechanism, and recording medium (not separately shown) for controlled recording of fingerprint images. Terminal 18 will include a keyboard (not separately shown) which is used by an operator to interface with fingerprinting system 10. Rolled fingerprint images generated by system 10 can be displayed on video monitor 26, or printed onto a standard fingerprint card by printer 28. Alarm 30 is activated when a fingerprint is not properly captured, providing the operator with an indication that the capture procedure must be repeated. A system similar to this is disclosed in Fishbine et al. U.S. Pat. No. 4,933,976, which is hereby incorporated by reference.

Optical devices such as finger prism 20 are well known and disclosed, for example, in the McMahon U.S. Pat. No. 3,975,711 and the White U.S. Pat. No. 3,200,701. Finger prisms of this type are also disclosed in U.S. Pat. Nos. 4,792,226 and 4,811,414, which are assigned to the same assignee as the present invention. These devices utilize the optical principle of total internal reflection. When a finger is positioned on finger receiving surface 34 (a planar surface in the preferred embodiment but a curved surface could be used, mitigating the necessity of rolling the fingers), an optical image of the ridge and valley pattern on the surface of the finger (i.e., the fingerprint) is propagated from image propagation surface 32. Other means or optical devices which provide fingerprint images can also be used.

Figure 2A:
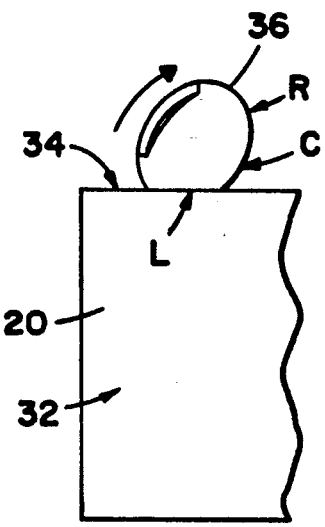
FIGS. 2A-2C show several portions of a finger in contact with the prism shown in FIG. 1, as the finger is rolled across the prism during a fingerprint capture operation.
Figure 3A:
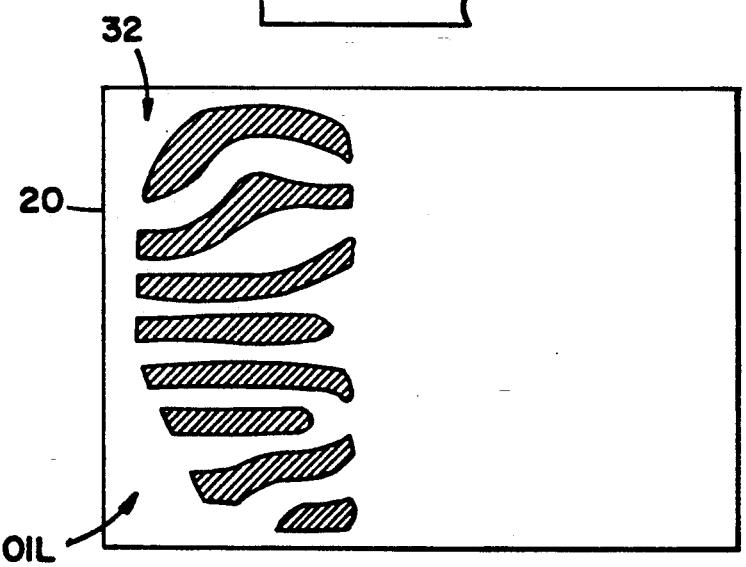
FIGS. 3A-3C illustrate an optical image of the fingerprint of the portions of the finger in contact with the prism in FIGS. 2A-2C, respectively.
Figure 2B:
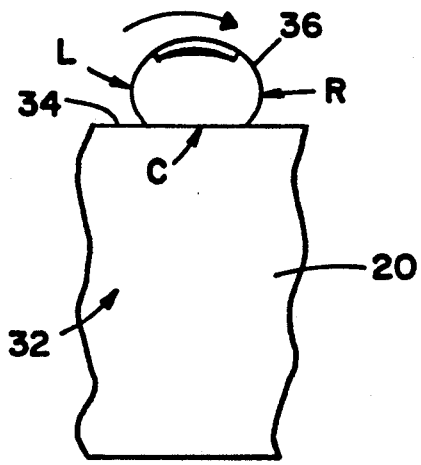
Figure 3B:
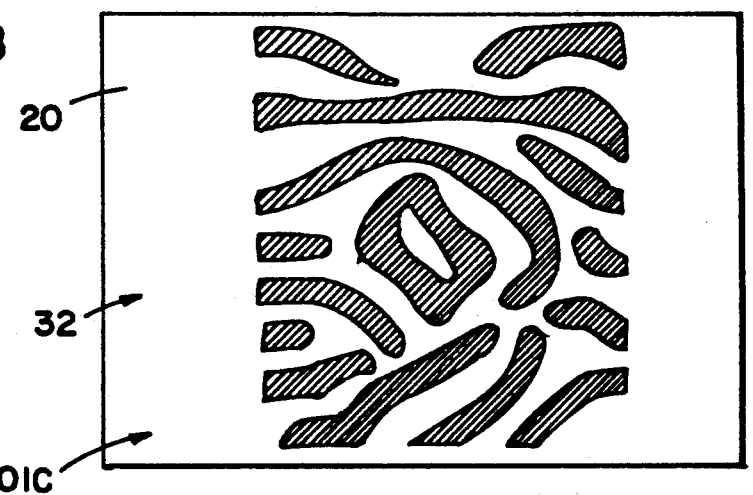
Figure 2C:
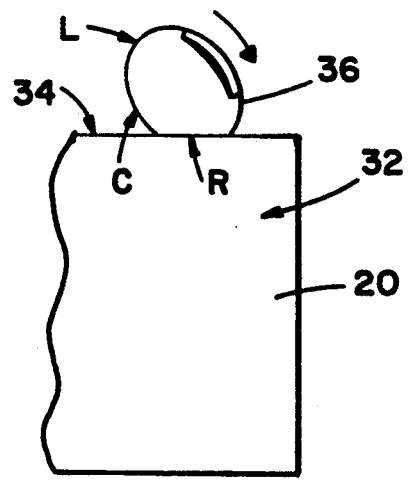
Figure 3C:
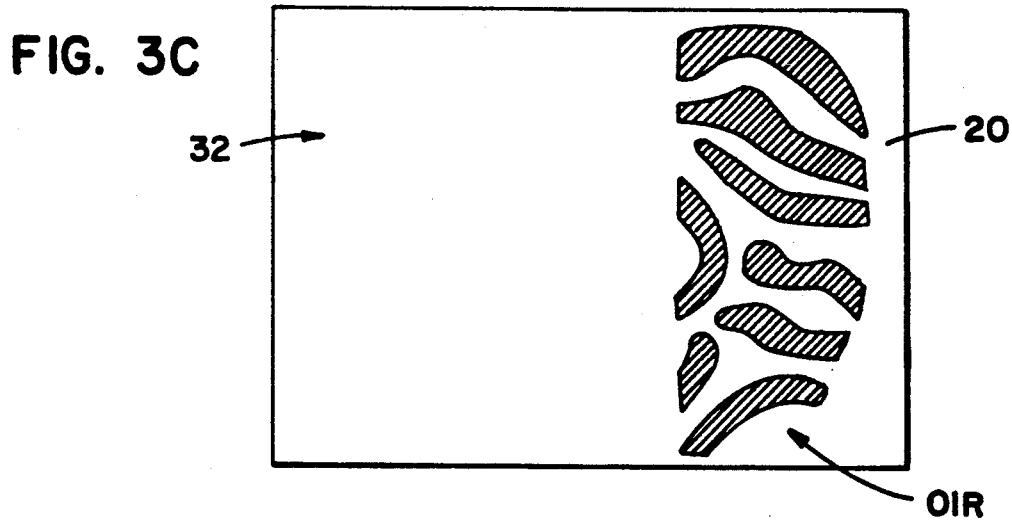
Figure 6:
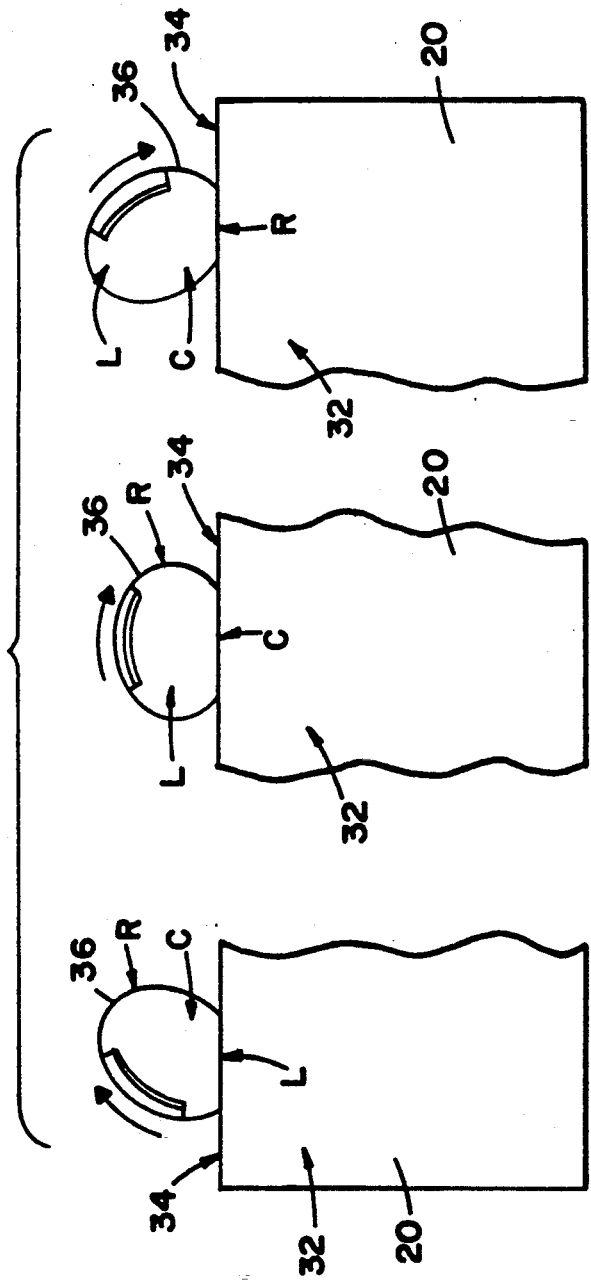
FIG. 6 is a sequence of illustrations showing the finger being rolled across the prism.

A person to be fingerprinted will position a first edge portion of their finger 36 on the receiving surface 34 of prism 20, and roll the finger to the opposite or second edge. In the example illustrated sequentially in FIG. 6, finger 36 is rolled in clockwise direction to the right from left edge L, through center portion C, to right edge R. (In this example, the images of the finger are presented as discrete samples. This is done for purposes of clarity in the explanation. In reality, light from the optical device will be projected continuously onto the image recording medium.) Portions L, C, and R of finger 36 are illustrated in contact with receiving surface 34, in FIGS. 2A-2C, respectively. Since the surface of finger 36 to be fingerprinted is curved, the area of contact between the finger and receiving surface 34, and therefore the fingerprint image of the portion of the finger in contact with the surface, will move with respect to prism 20 in the direction the finger is rotated. As finger 36 is rolled across prism 20 in the clockwise manner shown in FIGS. 2A-2C, the fingerprint images of finger portions L, C, and R will move from left to right across image propagation surface 32. Optical images OIL, OIC and OIR, which are propagated from image propagation surface 32 as portions L, C and R of finger 36 contact finger receiving surface 34, respectively, are illustrated in FIGS. 3A-3C.

Figure 4A:
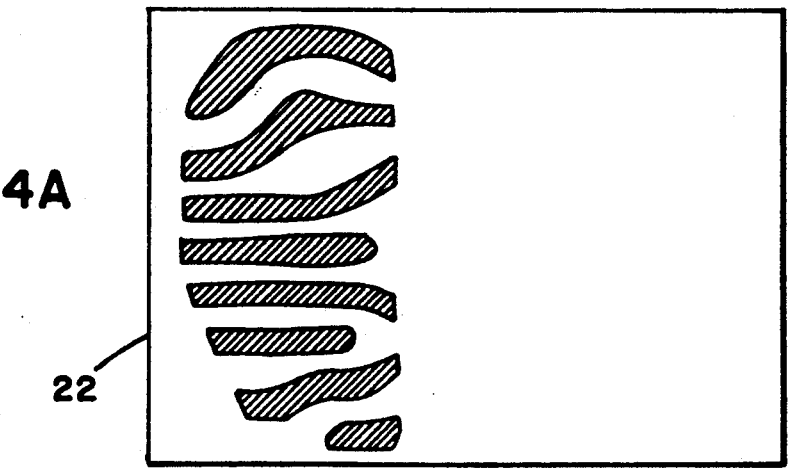
FIGS. 4A-4C illustrate the rolled fingerprint image on the image recording medium as the optical images of FIGS. 3A-3C are recorded.
Figure 4B:
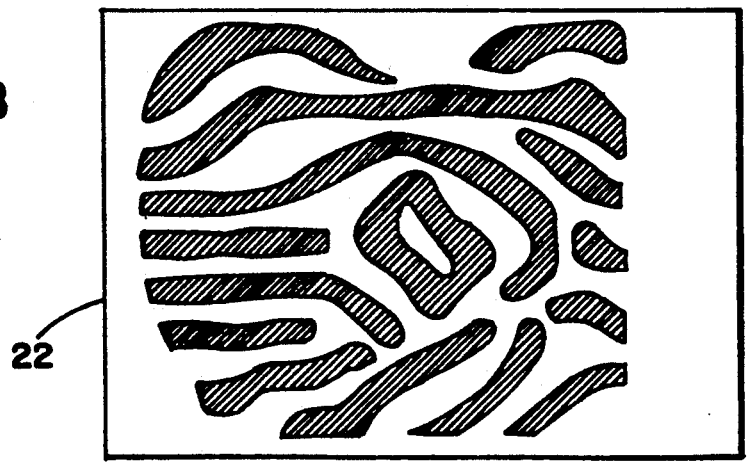
Figure 4C:
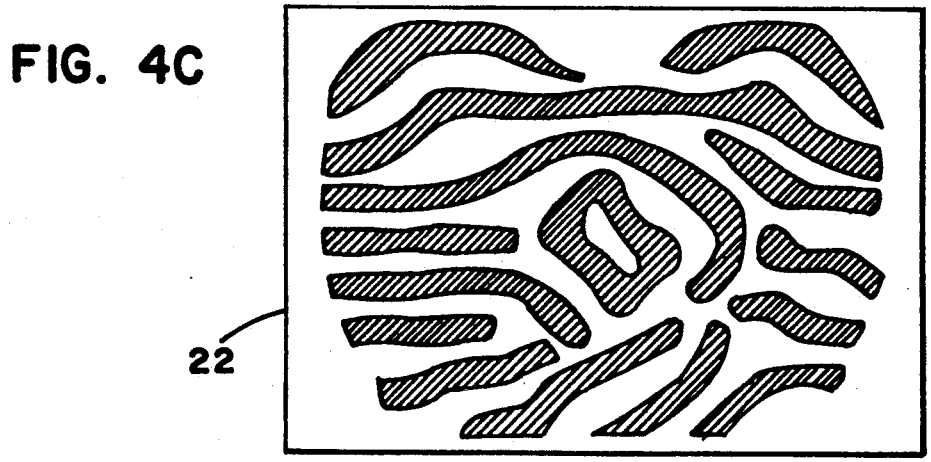

Image recorder 22 is mounted with respect to prism 20 and configured in such a manner that its field of view encompasses the entire image propagation surface 32. Image recorder 22 continuously images fingerprint images such as OIL, OIC and OIR through its objective lens onto its image recording medium, resulting in an image representative of the accumulation of the light reflected from the parts of the finger in contact with the surface, illustrated in FIGS. 4A-4C. (Again, the recorded image is shown to grow in discrete steps. In reality, the recorded image will appear to grow from left to right as the finger rolls.) Digitizer 24 is connected to image recorder 22, and digitizes the resulting image.

In the preferred embodiment of system 10, image recorder 22 is made up of a standard 50 mm camera lens 44 and a commercially available, electronically shuttered, high-latency CCD array device 40 (such as Thomson Composants Militaires et Spatiaux of France component number TH 7866 Area Array CCD Sensor) adapted to integrate images over the desired period of time (typically 1-3 seconds). In the preferred embodiment, prism 20 has one side painted black (to present a black background) and a light source 42 is positioned such that parts of the finger in contact with receiving surface 34 appear as a source of light to the image recorder. The recorded image looks like the photographic negative of the rolled fingerprint image. Digitizer 24 is integrated into the CCD array device such that, on command from the processor 12, the image stored in the CCD array device is converted to a digital stream of data representing the rolled fingerprint image, sent to processor 12 and stored in RAM 14. A monochromatic light source 42 and filter 38 can be used to reduce the effects of stray photons on the rolled fingerprint image.

In a second embodiment of system 10, image recorder 22 is a video camera that continuously images fingerprint images such as OIL, OIC, and OIR through its objective lens, and generates frames of video signals representative thereof. Commercially available video cameras using conventional rasters and scanning rates can be used. In this embodiment, digitizer 24 is a frame grabber. The frame grabber implements in hardware a conventional "video keying" method. In the preferred embodiment described herein, digitizer 24 implements in hardware a circuit which performs a selective replacement of pixel values stored in RAM 14. Each pixel extracted from camera 22 has a unique corresponding value stored in RAM 14. Prior to the initiation of image capture from camera 22, all pixel values in RAM 14 are pre-set to a common intensity value which represents the blackest value. As each pixel value is extracted from camera 22 and digitized by digitizer 24, its digitized value is directly compared with the corresponding pixel value stored in RAM 14. If the digitized value is brighter, then it's value replaces the corresponding value in RAM 14. Otherwise its value is ignored. Where commercially available video cameras and video monitors are employed, this embodiment provides the additional advantage of permitting the operator of the equipment to view the roll of the fingerprint in real time.

Other image recording media 40, such as film, and other imaging systems, such as electrophotography, can be used. For purposes of example, if the recording media 40 is a light-sensitive light-emitting phosphor, exposure of the media results in a long persistence image of the rolled fingerprint. This long persistence provides the additional time to scan the corresponding fingerprint image. The scan, conducted by a single photodetector, or a vector of photodetectors, is thereby permitted additional time to digitize the corresponding image at any desired optical resolution.

In the preferred embodiment described herein, digitizer 24 is controlled by processor 12 such that the image stored in the CCD array is read to the processor 12. The digitizer produces two-dimensional arrays of digital pixel values $PV_{n,m}$ representative of the intensity of the rolled fingerprint image at corresponding discrete pixel locations $PL_{n,m}$. In one embodiment digitizer 24 causes the image arrays to be formed of $N=480$ rows by $M=640$ columns of pixel values. For purposes of example, image arrays such as shown in FIG. 5 having 20 by 28 pixel values $PV_{n,m}$ are used throughout this description.

The pixel values $PV_{n,m}$ must have sufficient dynamic range to fully represent the rolled fingerprint image. In one embodiment, frame digitizer 24 includes an eight bit analog-to-digital converter which converts the video signals to eight bit pixel values $PV_{n,m}$ characteristic of rolled fingerprint image intensity. In this embodiment an eight bit pixel value $PV_{n,m}$ representative of a decimal zero (i.e., "00000000") is a minimum pixel value PVMIN and characterizes a lowest intensity or blackest pixel location $PL_{n,m}$. A pixel value representative of a decimal two hundred and fifty-five (i.e. "11111111") is a maximum pixel value PVMAX and represents a highest intensity or whitest pixel location of $PL_{n,m}$. A pixel value $PV_{n,m}$ representative of a decimal one hundred and twenty-eight (i.e. "10000000") represents a pixel location $PL_{n,m}$ having an intensity halfway between the lowest and highest intensities (i.e. grey).

For purposes of example, pixel values $PV_{n,m}$ are represented as being either white or black in the drawing figures accompanying this description. When finger 36 is not positioned on prism 20, pixel values $PV_{n,m}$ characteristic of the resulting background image will all be in the range of either PVMAX or PVMIN. When finger 36 is positioned on prism 20, ridges of the fingerprint will contact the prism, and pixel values $PV_{n,m}$ will be in the range of the other of PVMAX and PVMIN. In the embodiment of system 10 used for purposes of example throughout this description, lighter portions of optical images such as OIL characterize portions of finger 36 in contact with prism 20 (i.e. the ridges) and will be represented by pixel values $PV_{n,m}$ having magnitudes approaching PVMAX. The background and valleys of finger 36 in this embodiment are characterized by darker portions of images such as OIL, and are represented by pixel values $PV_{n,m}$ having magnitudes approaching PVMIN.

Processor 12 determines the presence or absence of an object on receiving surface 34. In one embodiment, processor 12 commands digitizer 24 to digitize the image from the image recording medium. The lack of significant change in pixel values is an indication that there is no object present. In other embodiments, a photodiode in the image recorder or a pressure switch on receiving surface 34 will notify processor 12 when an object makes contact with the receiving surface. The processor uses knowledge of the presence or absence of an object on the receiving surface to "timeout" and set alarm 30 if no object is present within a predetermined time after the start of the fingerprint "capture" and also to terminate the fingerprint capture process when the finger is removed. This "timeout" knowledge can also be used to reset the shutter state of the camera and thereby prevent overexposure of the recording media in the event of a long interval between the beginning of image recording and the onset of actual image.

When it is desired to capture a rolled fingerprint image, the operator will actuate a foot pedal (not shown) or a key on terminal 18 to place system 10 in a capture mode. Assuming left portion L of finger 36 is positioned on finger receiving surface 34 of prism 20 after the capture mode is entered, its optical image OIL will be propagated from the prism and recorded by image recorder 22. Then, as the finger rolls from left to right, the image recorder will continuously record the light propagating from the entire image propagation surface 32. After the completion of the finger roll, the finger is removed from the finger receiving surface. The removal of the finger, in turn, terminates the fingerprint capture process and the rolled fingerprint image is stored to RAM 14. The digitized array (shown in FIG. 5) will include pixel values $PV_{n,m}$ representative of a rolled fingerprint taken from finger 36. Before being displayed on video monitor 26 or onto an applicant card by printer 28, pixel values $PV_{n,m}$ can also be processed in accordance with methods described in the above referenced U.S. Pat. No. 4,811,414.

Although the present invention has been described with reference to the preferred embodiments, those skilled in the art will recognize that changes may be made in form and detail without departing from the spirit and scope of the invention.

What is claimed is:

1. An identification image recording apparatus, comprising:

prism means for propagating light corresponding to raised surfaces of a portion of a human body in contact with the prism means, wherein the prism means comprises a light source and a prism, the prism having a receiving surface and a light propagating surface, wherein the receiving surface has reflective properties which change as a function of contact with the human body portion and wherein the light propagating surface propagates light reflected from the receiving surface, the prism and the light source being configured so that propagated light corresponding to areas of the receiving surface in contact with the raised surfaces is higher in intensity than propagated light corresponding to other areas of the receiving surface;

image recording means positioned to continuously receive the propagated light, wherein the image recording means comprises an image recording medium for accumulating the light over a period of time corresponding to a complete finger roll to form a skin print image;

conversion means for converting said skin print image into electrical signals; and image processing means connected to said image recording means for receiving said electrical signals.

2. The apparatus according to claim 1 wherein the image recording medium comprises a CCD array positioned to continuously receive said propagated light.

3. The apparatus according to claim 2 wherein the conversion means includes means for reading the CCD array.

4. The apparatus according to claim 1 wherein the conversion means includes means for storing the skin print image in memory.

5. The apparatus according to claim 1 wherein the image recording medium comprises an electrophotographic recording system.

6. The apparatus according to claim 1 wherein said prism means further comprises monochromatic filters positioned between the image recording means and the propagating surface of the prism.

7. A method of generating data characteristic of a rolled fingerprint image, wherein the method comprises the steps of:
providing an optical device having a finger receiving surface which reflects light as a function of a ridge and valley pattern of a finger brought in contact with the finger receiving surface, a light propagating surface which propagates light reflected from the finger receiving surface and a source of illumination positioned to project light onto the receiving surface;
providing an image recording medium positioned to receive the propagated light;
placing a finger on the finger receiving surface of the optical device;
rolling the finger across the finger receiving surface, wherein the step of rolling occurs over a period of time;
continuously recording the rolled fingerprint image as the finger contacts the finger receiving surface, wherein the step of recording comprises accumulating on said image recording medium, during the period of time the finger is being rolled across the receiving surface, a fingerprint image which varies as a function of intensity of the propagated light over the period of time;
converting the fingerprint image into digital signals; and
generating an array of digital data characteristic of a complete rolled fingerprint image from the digital signals.

8. The method according to claim 7 wherein the step of generating the array includes generating the array in real time as the finger is being rolled.

9. The method according to claim 8 wherein the step of converting the fingerprint image includes determining a threshold value for the digital data to determine presence or absence of contact of the finger with the receiving surface.

10. The method according to claim 7 further including the steps of:
detecting that the finger is on the finger receiving surface; and
terminating the step of accumulating if the finger is not in contact with the finger receiving surface.

11. The method according to claim 10 further including the step of activating an alarm if the finger is not detected within a preselected amount of time from the start of image recording.

12. A method of capturing a skin print image, wherein the method comprises the steps of:
providing an optical device having a receiving surface which reflects light as a function of a ridge and valley pattern in skin brought in contact with the receiving surface, a light propagating surface which propagates light reflected from the receiving surface and a source of illumination positioned to project light onto the receiving surface;
providing an image recording medium positioned to receive the propagated light;
placing a portion of a human body in contact with the receiving surface;
reflecting light projected from the illumination source off the receiving surface;
propagating the reflected light through the propagating surface;
accumulating a first image as a function of intensity of the propagated light over a first period of time;
accumulating a second image as a function of intensity of the propagated light over a second, nonoverlapping, period of time; and
combining the first and second images to form the skin print image.

13. The method according to claim 12 wherein the step of combining comprises the steps of:
digitizing the first and second images to form first and second arrays of pixels, respectively, wherein each pixel has an intensity value;
adding the pixel intensity values of the first and second pixels arrays to produce a third pixel array; and
storing the third pixel array as the skin print image.

14. A method of generating data characteristic of a rolled fingerprint image, wherein the method comprises the steps of:
providing an optical device having a finger receiving surface which reflects light as a function of a ridge and valley pattern of a finger brought in contact with the finger receiving surface, a light propagating surface which propagates light reflected from the finger receiving surface and a source of illumination positioned to project light onto the receiving surface;
providing an image recording medium positioned to receive the propagated light;
placing a finger on the finger receiving surface of the optical device;
rolling the finger across the finger receiving surface, wherein the step of rolling occurs over a period of time;
continuously recording the rolled fingerprint image as the finger contacts the finger receiving surface, wherein the step of recording comprises accumulating on said image recording medium, during the period of time the finger is being rolled across the receiving surface, a rolled fingerprint image which varies as a function of intensity of the propagated light over the period of time.

15. The method according to claim 14 wherein the step of recording further comprises the steps of:
converting the fingerprint image into digital signals; and
generating an array of digital data characteristic of the rolled fingerprint image from the digital signals.

* * * * *